US008856975B2

(12) United States Patent
Lang et al.

(10) Patent No.: US 8,856,975 B2
(45) Date of Patent: Oct. 14, 2014

(54) HEADBAND DEVICE FOR AN OXYGEN MASK, AND METHOD FOR THE PRODUCTION THEREOF

(75) Inventors: Bernd Lang, Gräfelfing (DE); Achim Biener, Aufkirchen (DE); Martin Bechtel, Winsen/Luhe (DE); Harald Vögele, Gauting (DE); Caspar Graf Stauffenberg, Gauting (DE)

(73) Assignee: ResMed R&D Germany GmbH, Martinsried (DE)

( * ) Notice: Subject to any disclaimer, the term of this patent is extended or adjusted under 35 U.S.C. 154(b) by 0 days.

(21) Appl. No.: 13/367,798

(22) Filed: Feb. 7, 2012

(65) Prior Publication Data
US 2012/0145157 A1 Jun. 14, 2012

Related U.S. Application Data

(63) Continuation of application No. 10/578,864, filed as application No. PCT/EP2004/012811 on Nov. 11, 2004, now Pat. No. 8,132,270.

(30) Foreign Application Priority Data

Nov. 11, 2003 (DE) .................................. 103 52 607
Nov. 11, 2003 (DE) .................................. 103 52 608

(51) Int. Cl.
*A42B 1/22* (2006.01)
*A61M 16/06* (2006.01)
(52) U.S. Cl.
CPC ....... *A61M 16/0683* (2013.01); *A61M 16/0633* (2014.02); *A61M 2016/0661* (2013.01)
USPC .......................................... 2/420; 128/207.11
(58) Field of Classification Search
USPC .......... 2/417–420, 452; 128/201.22–24, 0.27, 128/206.21, 206.24, 206.28, 128/207.11–207.13, 0.17, 112.1, 857
See application file for complete search history.

(56) References Cited

U.S. PATENT DOCUMENTS 3,013,556 A 12/1961 Galleher
4,367,735 A 1/1983 Dali
(Continued)

FOREIGN PATENT DOCUMENTS

CN 1326371 A 12/2001
CN 1408453 A 4/2003
(Continued)

OTHER PUBLICATIONS

International Search Report for PCT/EP2004/012811 dated Apr. 12, 2005.
(Continued)

*Primary Examiner* — Katherine Moran
(74) *Attorney, Agent, or Firm* — Nixon & Vanderhye P.C.

(57) ABSTRACT

The invention relates to a headband means (1) used for applying a breathing mask (2) in a user's facial area. Said headband means (1) comprises a flexible band body that is provided with upper and lower band portions (3, 4) and is used for transmitting the mask holding forces required for applying the breathing mask. At least some portions of the band body are made of a foamed plastic material. The invention further relates to an application device (102) for a breathing mask, comprising a headband means which extends around the back of a user's head. The headband means encompasses a supporting structure (S) made of a material that can at least once be temporarily brought into a state in which at least some portions of the headband means can be individually adjusted to the shape of the back of the user's head.

46 Claims, 6 Drawing Sheets

(56) References Cited

U.S. PATENT DOCUMENTS

| | | | |
|---|---|---|---|
| 4,675,919 | A | 6/1987 | Heine et al. |
| 5,265,595 | A | 11/1993 | Rudolph |
| 5,542,128 | A | 8/1996 | Lomas |
| 5,724,677 | A | 3/1998 | Bryant et al. |
| 5,829,062 | A | 11/1998 | Magidson |
| 6,470,886 | B1 | 10/2002 | Jestrabek-Hart |
| 2004/0025882 | A1* | 2/2004 | Madaus et al. .......... 128/206.27 |
| 2007/0130663 | A1 | 6/2007 | Lang et al. |
| 2007/0209663 | A1 | 9/2007 | Marque et al. |

FOREIGN PATENT DOCUMENTS

| | | |
|---|---|---|
| DE | 198 07 961 A1 | 8/1999 |
| DE | 100 35 946 | 2/2002 |
| EP | 1 356 843 | 10/2003 |
| FR | 2 658 725 | 8/1991 |
| JP | A-2000-135103 | 5/2000 |
| WO | WO 00/50122 | 8/2000 |
| WO | WO 02/07806 | 1/2002 |
| WO | WO 02/47749 | 6/2002 |

OTHER PUBLICATIONS

Translation of Office Action from corresponding Chinese Patent Application No. 2004800402201.
Chinese Office Action and English Translation for co-pending Chinese Application No. 2004800402201, dated May 22, 2009, 7 pages.
Office Action issued in Japanese Appln. No. 2006-538801, mailed Jan. 26, 2010, w/English translation.
European Search Report issued in EP Appln, No. 11170495.3 (Nov. 7, 2011).
Office Action issued in a corresponding German Application No. 103 52 608.0, dated Jan. 21, 2013, with English translation thereof.
Office Action issued in corresponding Chinese Application No. 201010260432.8 on Dec. 31, 2013 with partial English-language translation.

\* cited by examiner

HEADBAND DEVICE FOR AN OXYGEN MASK, AND METHOD FOR THE PRODUCTION THEREOF

This application is a continuation of U.S. application Ser. No. 10/578,864, filed Jun. 22, 2006, which is the U.S. national phase of international application PCT/EP2004/012811 filed 11 Nov. 2004, which designated the U.S. and claims priority to DE 103 52 608.0 filed 11 Nov. 2003, and DE 103 52 607.2 filed 11 Nov. 2003, each of which is incorporated herein by reference in its entirety.

The present invention relates to a headband means for applying a breathing mask in a user's facial area. Furthermore, the present invention also relates to a method for producing a headband means of this kind. The present invention moreover relates to an application means for a breathing mask comprising a headband.

Breathing masks are used particularly in the medical and therapeutical sectors for treating sleep-related respiratory disorders. Breathing masks of this kind make it possible to supply a user with a breathable gas, in particular filtered ambient air, on a pressure level which lies above the ambient pressure. This respiratory gas supply, which is carried out at an increased pressure, makes it possible to achieve a pneumatic splinting in the area of the upper respiratory passages in order to thus prevent possible obstructions in the area of these respiratory passages. The breathing masks which are used in such a manner for treating sleep-related respiratory disorders are worn by the user during the entire rest and sleep periods. These breathing masks are normally fixed to the head of the user by means of a headband arrangement. These headband arrangements can comprise an upper headband portion as well as a lower headband portion, wherein the upper headband portion exerts corresponding holding forces on a forehead supporting means of the breathing mask. The breathing mask can be forced by the lower headband portion against the area surrounding the nose, the nose bridge area as well as the area of the upper lip.

It is the object of the present invention to provide a headband means which can be produced advantageously in view of production engineering and which stands out due to a high wearing and using comfort.

In accordance with a first attempt, this object is achieved with a headband means for applying a breathing mask to a user and comprising a flexible band body having upper and lower band portions for transmitting the mask holding forces required for applying the breathing mask, wherein at least portions of the band body are made of a foamed plastic material.

It is thus advantageously possible to produce a headband means which stands out due to its cushioning characteristics without considerable cutting losses as a mass-produced article.

In accordance with a particularly preferred embodiment of the present invention, the plastic material that is intended for forming the band body is molded to become the band body by injecting the plastic material into a corresponding mold space. The band body is advantageously configured such that it has a skin in the area of its outer surfaces. This skin effect can be achieved by providing the corresponding inner space of the mold with a coating. The coating can be made, in particular, in a powder coating process or by inserting films.

In accordance with a particularly preferred embodiment of the present invention, the band body is provided with a tensile stiff insert. This tensile stiff insert is preferably made of a thermoplastic material, in particular a nylon or polyamide material. At least portions of the insert included in the band body can be configured such that in portions it forms a dimensionally stable insert. The cushioning properties, in particular the cushion thickness of the band body can vary such that particularly in band zones with increased contact pressure the cushion is thicker.

In accordance with a particularly preferred embodiment of the present invention, the band body comprises closure means for coupling a band strap or bracket portion or mask fixing elements in an adjustable manner. It is thus possible to adjust the mask contact pressure precisely by means of the headband means. The closure means preferably have a locking structure that is formed integrally with the headband means. The locking structure can be configured such that a locking effect can be achieved on the basis of a force and/or a form-fit coupling with a corresponding counter structure. It is possible to configure the locking structure such that it is formed in particular integrally with the insert that receives tensile forces or is tensile proof. The tensile proof insert can be configured such that it exhibits a specific bending behavior. This specific bending behavior can be achieved in particular by forming recesses in the tensile proof insert as well as by adjusting the thickness of the tensile proof insert.

In accordance with a particularly preferred embodiment of the present invention, the closure means comprise a slide means which can be locked on the headband means in different closing positions. The slide means can comprise a locking mechanism for locking the slide means on the locking structure.

In accordance with a further aspect of the present invention, the above-mentioned object is also achieved by a process for producing a headband means in which, within the scope of a first plastic injection step for forming a tensile stiff insert, a corresponding plastic material is injected into a molding tool space configured so as to form the insert, and within the scope of a subsequent plastic injection step, a pore-forming plastic material is injected in an enlarged mold space in such a manner that the pore-forming material covers the tensile proof insert at least partially so as to form a cushion portion.

The present invention moreover relates to an application device for a breathing mask, in particular for breathing masks for treating sleep-related respiratory disorders.

In this regard, it is the object of the present invention to provide an application device for a breathing mask which allows a reliable fixing of a breathing mask and which stands out due to a high using comfort.

In accordance with the present invention, this object is achieved with an application device for a breathing mask comprising a headband means which extends in the application position around the back of a user's head, wherein the headband means comprises a supporting structure, and this supporting structure is made of a material which can at least once be brought temporally in a state in which the headband arrangement is at least in portions individually adaptable to the shape of the back of the user's head.

It is thus advantageously possible to provide a headband arrangement which guarantees that the course of the headband portions which extend towards the breathing mask is advantageously adapted to the individual shape of the mask user's head. Furthermore, it is also particularly advantageously possible to introduce the tensile forces applied via the headband portions under a low surface pressure into the area of the back of the mask user's head.

The headband arrangement is preferably configured such that the supporting structure rests on the back of the user's head at the height of the ear or in the area of the end of the cervical vertebra.

In accordance with a particularly preferred embodiment of the present invention, the supporting structure is made of a material which is plastically deformable after having been heated to a temperature of preferably at least 30° C. The supporting structure can be heated, e.g., in a water bath or by means of hot air.

The supporting structure is preferably made of a plastic material, in particular a thermoplastic material. The supporting structure can be configured so as to form a stiffening layer which, in the not yet completely cured state, can, e.g., be adapted to the curvature of the back of the user's head. The supporting structure can comprise a cushion on the side which faces a user in the application position. This cushion can be formed of a foamed and/or nonwoven material.

In particular in case the supporting structure is configured as a curved plate element, the supporting structure has preferably openings. This increases the supporting structure's permeability to vapor and avoids an excess moistening of the headband means. It is possible to configure the supporting structure such that it is releasably coupled with the headband means. It is thus advantageously possible to separate the headband means from the supporting structure and to clean the headband means separately.

In accordance with a particularly preferred embodiment of the present invention, the supporting structure is configured so as to comprise arm portions which extend from a main supporting surface portion along the headband portions.

The supporting structure can be configured such that it comprises a lower edge portion having two lower legs which extend in the application position towards the cheekbone and/or in an area lying below the corresponding earlobe in order to guide lower band portions of the headband arrangement. It is thus advantageously possible to adjust the course of the lower headband portions across the cheek area of the user advantageously to the individual head shape.

In accordance with a further aspect of the present invention, the supporting structure is preferably configured such that it comprises an upper edge portion having two upper legs which extend from a starting zone in the neck area in a direction across the ear region.

Further details and features of the present invention can be taken from the following description in combination with the drawings in which FIG. 1a is a side view of a user with a breathing mask that is applied by means of the headband means according to the present invention;

FIG. 5a is a side view for explaining the cross-sectional profile of a band body with a locking means formed integrally therewith;

FIG. 5b is a slide means assigned to the structure according to FIG. 5a;

FIG. 6a is a further cross-sectional variant of a band body with a tensile stiff insert formed therein as well as locking means formed integrally with the tensile proof insert;

FIG. 6b is a sketch for explaining a slide means assigned to the locking means according to FIG. 6a;

Figure 1A:
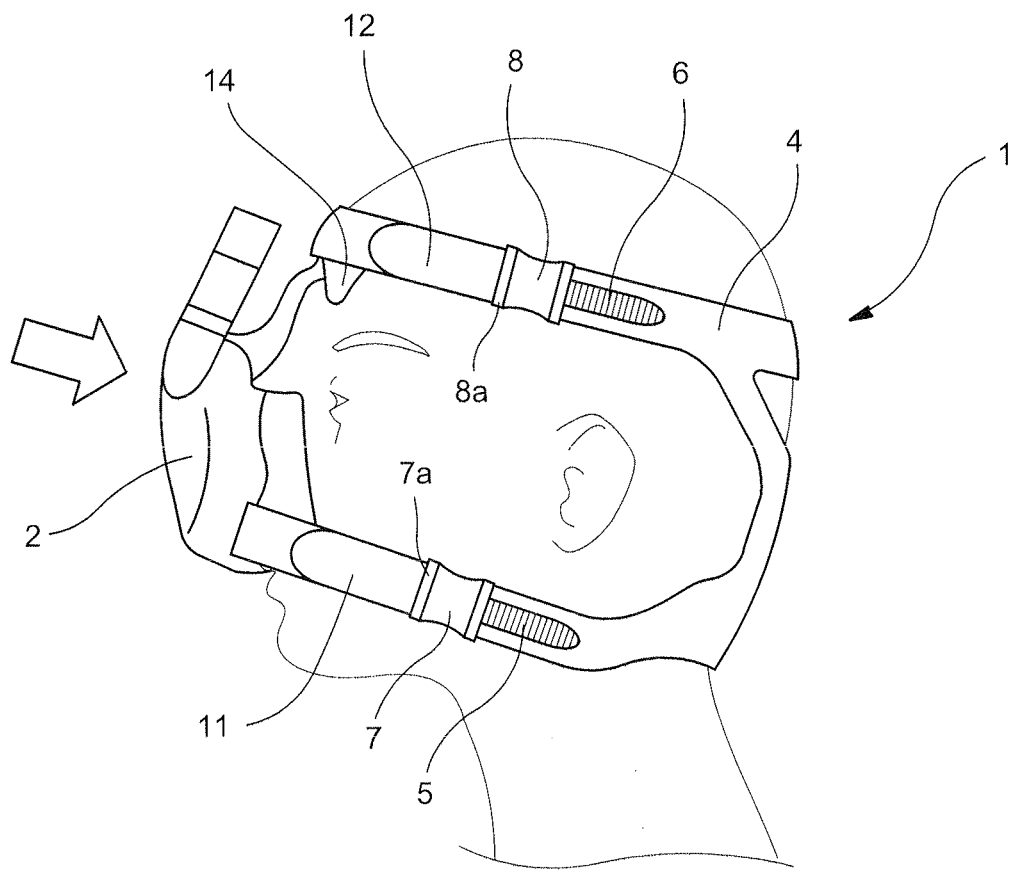
FIG. 1b is a sketch for explaining a headband means according to the present invention.

The breathing mask user shown in FIG. 1 wears a breathing mask 2 that is applied nasally by means of a headband means 1 according to the present invention. The breathing mask 2 is fixed by means of lower headband portions 3 and upper headband portions 4. The headband means 1 is made of a foamed plastic material by injecting the latter into a corresponding mold space portion within the scope of a plastic injection step.

The headband means 1 comprises locking means 5, 6 for attaching fixing means 7, 8 in an adjustable manner to the respective headband portion 3, 4. The fixing means 7, 8 have respective bracket or strap portions 7a, 8a, wherein further band portions 11, 12 extending towards the breathing mask 2 are passed through these bracket or strap portions 7a, 8a.

The headband means 1 is configured such that the lower headband portion 3 extends from the neck area, below the ears across the cheek area towards the breathing mask. The upper headband portion 4 extends from the area of the upper back of the head to the forehead area of the mask user. The lower headband portion 3 and the upper headband portion 4 provide the holding forces required for applying the breathing mask 2.

The lower headband portion 3 essentially determines the contact pressure between the breathing mask 2 and the area surrounding the nose of the mask user. The tensile force prevailing in the upper headband portion 4 essentially determines the contact pressure between a forehead supporting means 14 and the forehead of the mask user.

Figure 1B:
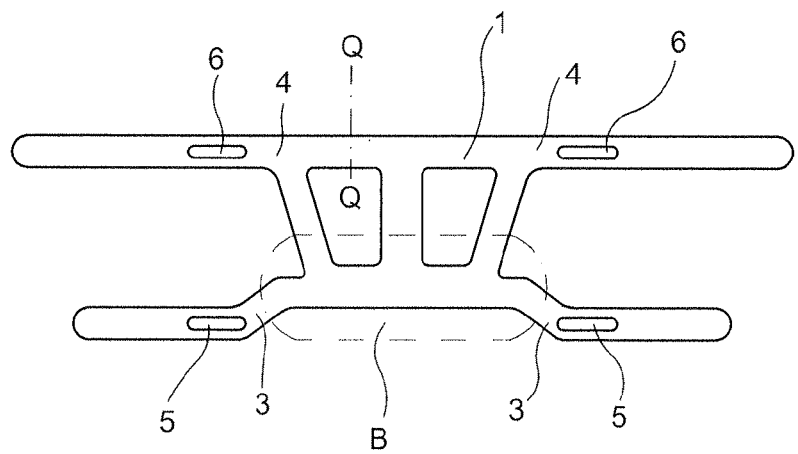

FIG. 1b schematically shows a headband means 1 that is spread out in a plane. This headband means comprises the upper headband portions 4 as well as the aforementioned lower headband portions 3. The headband means 1 is made of a foamed material and comprises a tensile proof insert. In the area B that is marked by dot-dash lines, the tensile stiff or tensile proof insert is configured such that it has a particularly high torsion stiffness around an axis extending essentially perpendicularly with respect to the supporting area. It is thus possible to bend the band in the area of the lower headband portions 3 or to realize an offset in this area so that the lower headband portions 3 can be advantageously passed below the ear area of the user towards his/her cheek area. As indicated, the headband means 1 is provided with locking structures 5, 6 which are formed integrally therewith and will be discussed below in more detail.

Figure 2:
FIG. 2 is a cross-sectional view of a band body without tensile stiff insert.

FIG. 2 shows an embodiment of the headband means according to the present invention which is entirely made of a pore-forming plastic material.

Figure 3:
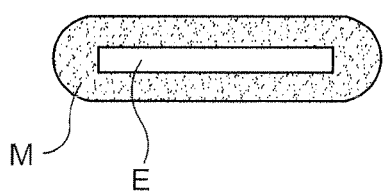
FIG. 3 is a cross-sectional view of a band body for explaining a variant with a tensile stiff insert.

FIG. 3 shows a cross-sectional sketch Q/Q for explaining a variant of the band body comprising a tensile stiff insert E. The tensile stiff insert is made of a thermoplastic material, for example nylon or polyamide. The tensile stiff insert E is embedded in a foam material M. The foam material M is injection molded to the tensile proof insert E.

Figure 4:
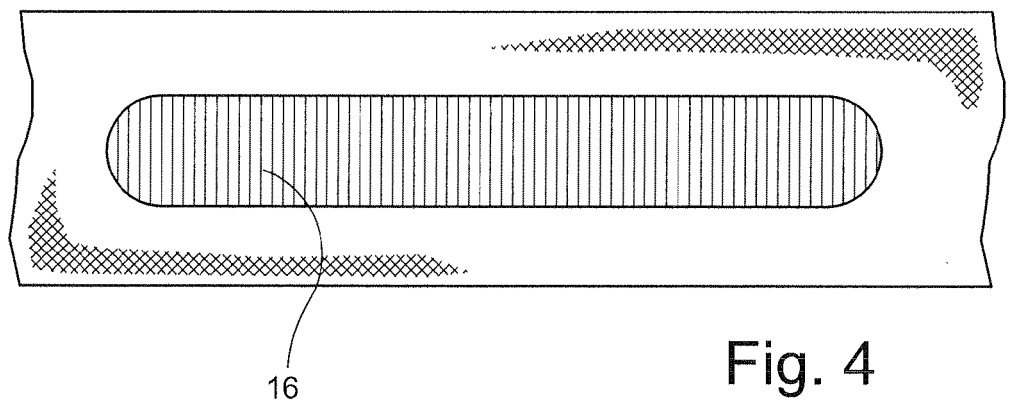
FIG. 4 is a sketch for explaining a locking portion that is formed on a headband according to the present invention.

FIG. 4 shows a sketch for explaining a locking structure 16 which is formed integrally with the tensile stiff or proof insert E in accordance with a particularly preferred embodiment of the present invention. The locking structure 16 is realized as a transversely interlocked web portion and can have, in particular, the cross section shown in FIG. 5a. The web body of the locking structure 16 is configured so as to form a guide means for a slide element. The locking position of the slide element on the web means is adjustable.

Figures 5A, 5B:
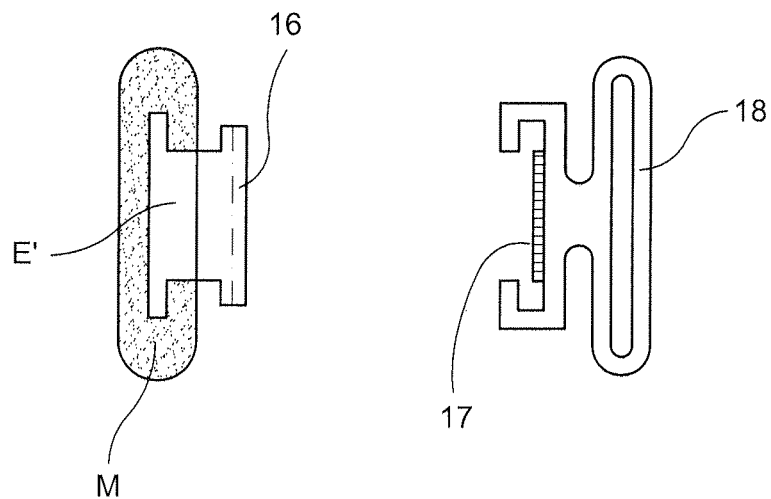

FIG. 5b schematically shows a possible variant of the slide element to be placed on the web means according to FIG. 5a or according to FIG. 4. The slide element comprises a locking mechanism 17 (not shown in detail) which can be selectively engaged with the locking structure 16. The slide element comprises a bracket or strap portion 18 for receiving a band portion 11, 12, as shown in FIG. 1a.

Figures 6A, 6B:
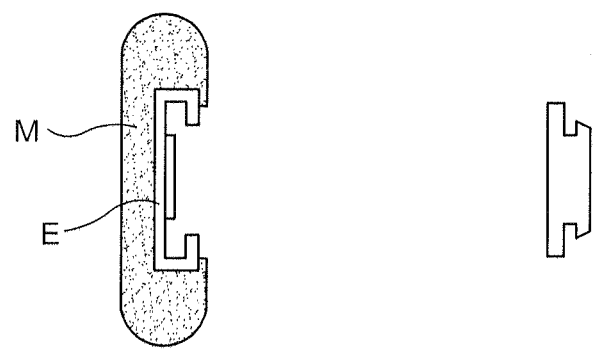

FIG. 6a shows a further cross-sectional variant of a headband means according to the present invention in the area of the locking means. Here too, the head band body comprises a cushion layer M made of a foamed material as well as a tensile proof insert E embedded therein. Here too, the tensile proof insert E forms part of a locking means which is received in the band body in an almost sunk-in manner, in contrast to the variant according to FIG. 5a. A slide element can be inserted into the web means that is sunk-in in the band body, wherein the slide means can be attached in an adjustable manner to the corresponding guiding mechanism by means of a locking mechanism that is also not shown in detail.

Figure 7:
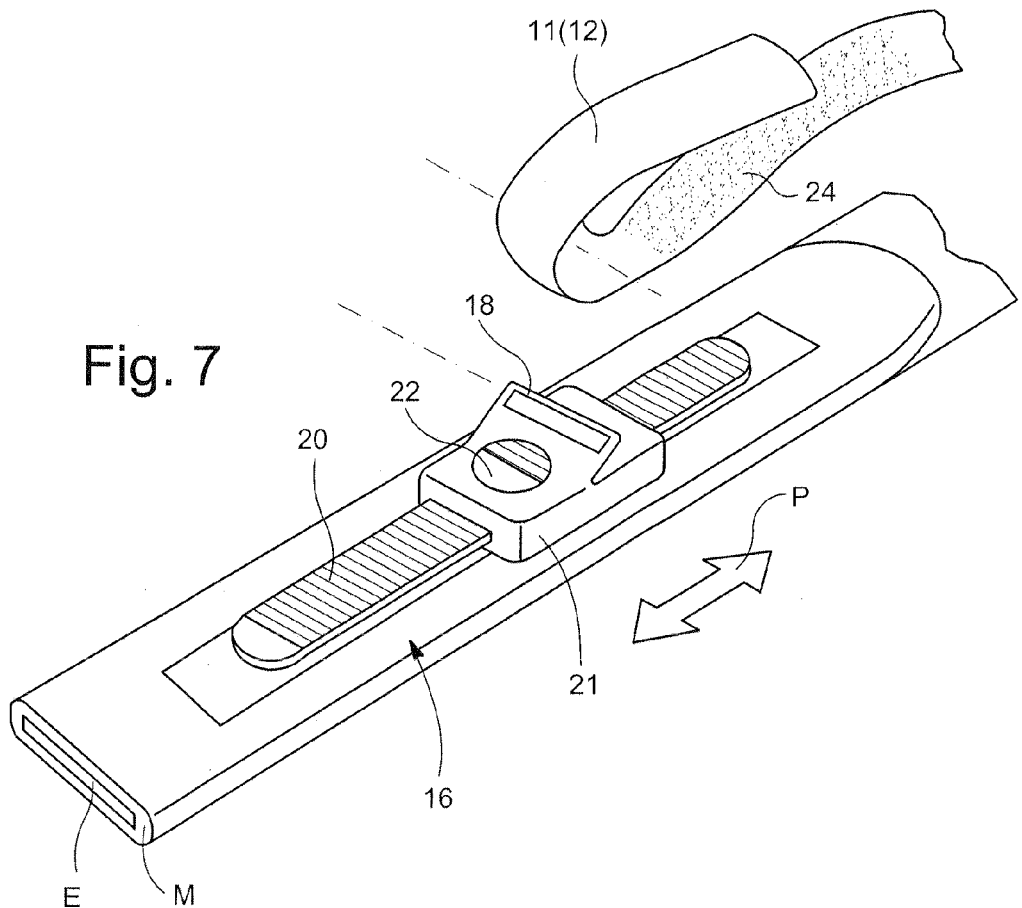
FIG. 7 is a perspective sketch for explaining further details of a headband for a breathing mask, wherein the headband is formed of a foamed material and comprises a tensile stiff insert and a locking means formed integrally therewith.
Figure 8:
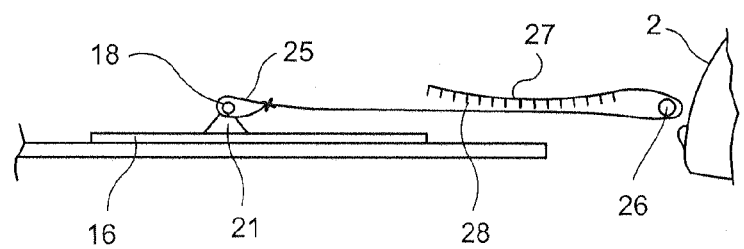
FIG. 8 is a sketch for further describing the function of the headband means according to FIG. 7.

FIG. 7 shows a headband variant comprising a cushion body M which is made of a foamed material and in which a tensile proof or stiff layer E is embedded. The tensile proof layer E comprises a locking means 16 which forms a guiding web having locking teeth 20. A slide element 21 is arranged on this guiding web. The slide element 21 can be moved in the directions shown by the arrow P by applying a pushbutton 22 which causes unlocking of the locking mechanism that is not shown in detail. The slide element 21 has a bracket or strap portion 18 through which a band portion 11, 12 of the headband means can be passed. The band portion 11, 12 is provided with a hook and loop fastener 24 for roughly and preliminarily adjusting the effective lengths of the corresponding headband portions 3, 4.

Alternatively to the shown attachment of the headband portion 11, 12 to the bracket portion 18, it is also possible to couple the slide element 21, as schematically shown in FIG. 18, with a breathing mask 2, namely in that the bracket portion 18 is embedded in a firmly sewn band bracket 25 and the attachment to the breathing mask 2 is realized by a band bracket 27 passed through a mounting bracket 26 of the breathing mask 2, wherein the band bracket 27 is realized by a hook and loop fastener 28 in a detachable manner. The slide element 21 can be moved along the locking means 16. The locking means 16 can also be realized by a web means that is sunk-in in the band body (FIG. 6a).

Figure 9:
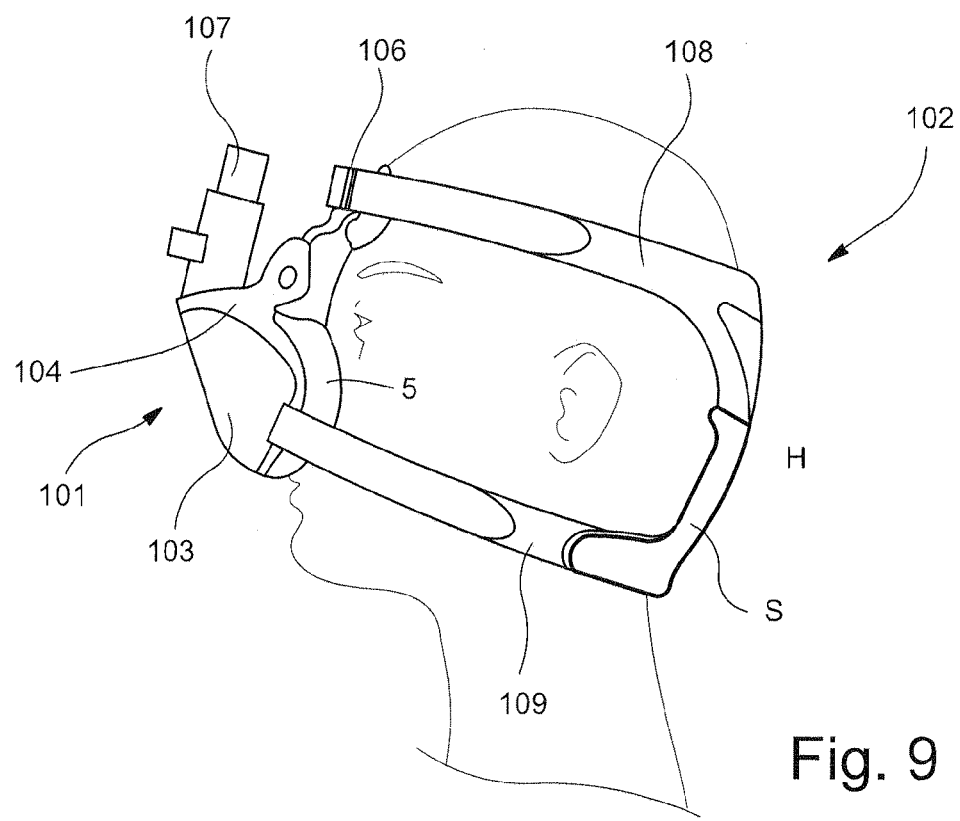
FIG. 9 is a side view of a breathing mask user with a breathing mask that is applied to the user by means of a headband arrangement.

FIG. 9 shows a breathing mask user to which a further breathing mask arrangement 101 is fixed by means of an application device 102 which, in the present embodiment, is realized as a headband arrangement. The breathing mask arrangement 101 comprises a mask base body 103 which rests on the nose area of the user and is sealed by a sealing lip 105. The mask base body 103 is fixed to the user by means of a frame structure and a forehead supporting means 106 coupled thereto. The respiratory gas can be supplied to the interior of the mask, which is defined by the mask base body 103, via the connection means 107 that is only shown schematically.

The application device 102 comprises an upper headband portion 108 which extends from the area of the back of the head H in the area of the forehead supporting means 106. Furthermore, the application device also comprises a lower headband portion 109 which extends from the neck area of the user across his/her cheekbones in the area of the mask base body 103. In this embodiment, the corresponding headband portion 108, 109 is coupled with the breathing mask arrangement 101 by means of hook and loop fastener structures which will be described in the following in connection with FIG. 11. The application device is provided with a supporting structure S which, in the present embodiment, is formed by a dimensionally stable plate material. The dimensionally stable plate material is made of a material which is plastically deformable under specific conditions and can thus be adapted to the individual shape of the back of the user's head. In this embodiment, the adaptability is achieved in that the material intended for forming the supporting structure is a thermodeformable plastic material. The material properties of this plastic material are adjusted such that this material is plastically deformable at temperatures in the range starting from about 50° C. By using the supporting structure that is adapted to the individual shape of the back of the head in accordance with the present invention, it becomes possible to apply the holding forces required for applying the breathing mask arrangement 101 in a manner which is advantageous in view of physiology. By adapting the supporting structure S to the individual shape of the user's head, it is in particular possible to determine the course of the lower headband arrangement 109 advantageously and, furthermore, achieve a high resistance against slipping and twisting.

Figure 10:
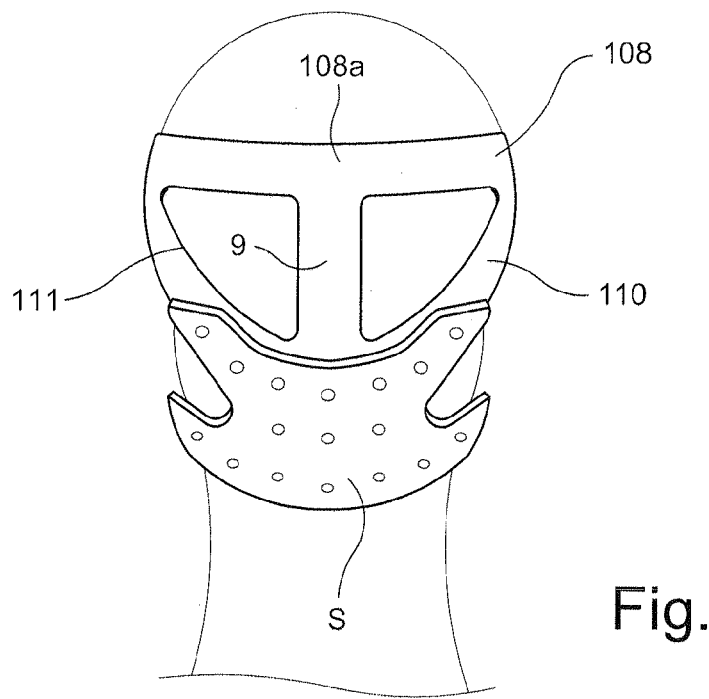
FIG. 10 is a view of the area of the back of the mask user's head for explaining a preferred shape of the headband arrangement in this area.

FIG. 10 is a rear view of the application device described above. It is evident from this view that the upper headband portion 8 is passed across the area of the back of the user's head. The portion 8a of the upper headband portion which bridges the area of the back of the head is coupled with the lower band arrangement of the application device 102, which extends in the area of the back of the user's head, by means of a vertical web 9 as well as by means of diagonal webs 110, 111. The headband means comprises said supporting structure S in the area of the back of the patient's head. This supporting structure S is adapted to the individual shape of the back of the user's head. The supporting structure S has openings for achieving an increased permeability to vapor.

Figure 11:
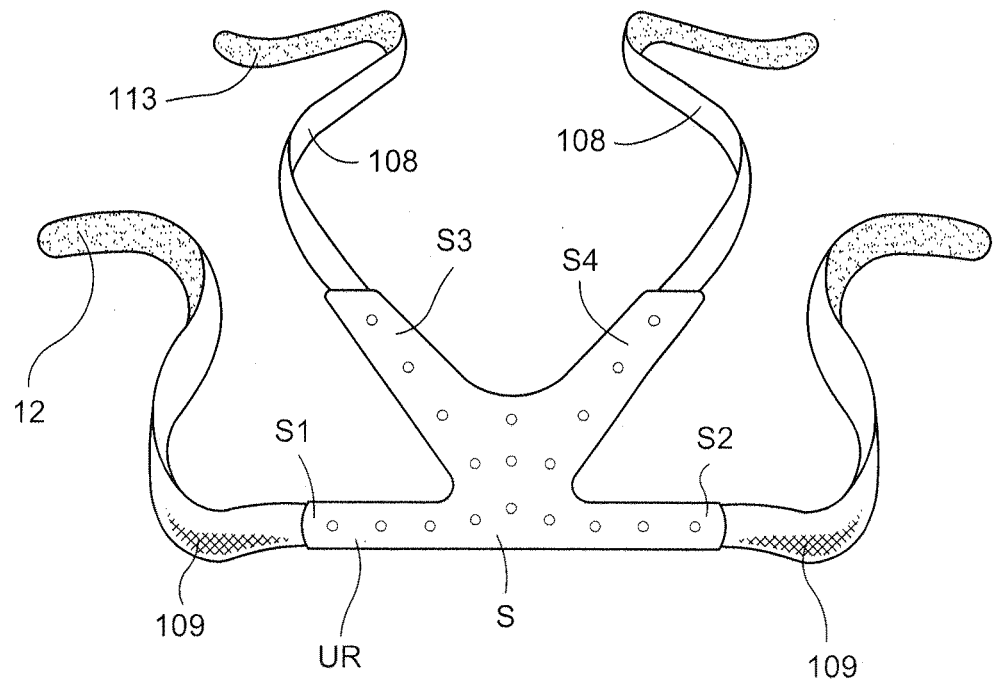
FIG. 11 is a sketch for explaining the configuration of an application device according to the present invention, which is separate from the breathing mask arrangement.

It is evident from FIG. 11 that the supporting structure S comprises a lower edge portion UR having leg portions S1, S2 which are arranged so as to guide the correspondingly assigned band portion 109 in such a manner that this band portion extends in an advantageous manner across the cheek area of the mask user. In this embodiment, the supporting structure comprises two further leg portions S3, S4 for guiding the upper band portions 108 of the headband means.

The headband portions 108, 109 are provided with hook and loop fasteners 112, 113 for detachably coupling the headband portions 8, 9 with corresponding bracket or strap portions of the breathing mask arrangement 101.

Figure 12:
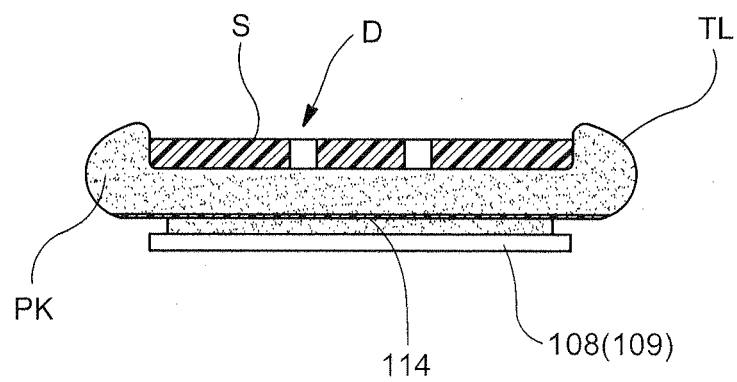
FIG. 12 is a sketch for explaining a preferred cross-sectional shape of the application device in the area of the supporting structure.

FIG. 12 is a simplified cross-sectional sketch showing a preferred embodiment of the application device in the area of the supporting structure S. The supporting structure S is provided with a cushion body PK. In this embodiment, the cushion body PK is formed of a foamed material which is embedded in a textile layer TL. The textile layer TL can be configured so as to provide a coupling surface 114 which makes it possible to couple the thus configured, cushioned supporting structure means detachably to the headband means 108, 109 by means of a hook and loop fastener. The supporting structure S has openings D for increasing its permeability to vapor.

The invention is not restricted to the embodiments described above. Alternatively to realizing the supporting structure S by a thermo-deformable material, it is also possible to make the supporting structure of a material which can be adapted to the shape of the back of the user's head in a different manner and which maintains this individual shape in a sufficiently dimensionally stable manner. In particular, this can be achieved by using curing materials, e.g. resins. The supporting structure S can be pre-shaped in such a manner that it has a curvature which takes into account the most probable shape of the back of the head, so that a further adaptation is possibly not required.

The concept of using a temporarily plastifiable dimensionally stable structure can be used advantageously in combination with the concept of forming the band body by foam injection molding, wherein the latter concept is also in accordance with the present invention. In particular, it is possible to make the tensile proof structures, which are mentioned in view of the foam injection molding concept, at least in the area of the back of the head of a material which is temporarily plastifiable, e.g. under the influence of heat, or which is at least sufficiently moldable.

The invention claimed is:

1. An application device for a breathing mask, comprising:
   a headband configured to support a breathing mask on a user's face, the headband including a cushion layer and a surface configured to contact the user's skin; and
   a supporting structure to facilitate the headband in supporting the breathing mask, the supporting structure comprising:
      a stiffening layer;
      a cushion located on an inner side of the supporting structure adapted to face the user in an application position; and
      a coupling surface including an attachment structure configured to releasably couple the supporting structure with the headband such that the supporting structure is configured to be removably attachable to the headband,
   wherein the supporting structure has a layered arrangement, and the cushion is positioned between the stiffening layer and the coupling surface.

2. The application device according to claim 1, wherein the supporting structure is configured to be located at a back of the user's head.

3. The application device according to claim 1, wherein the supporting structure is configured to be located at a height of the user's ear or in an area of an end of the user's cervical vertebra.

4. The application device according to claim 1, wherein the supporting structure is constructed of a material which is adaptable to an individual shape of a back of the user's head and which maintains the individual shape in a sufficiently dimensionally stable manner.

5. The application device according to claim 1, wherein the supporting structure is at least partially plastically deformable under specific conditions.

6. The application device according to claim 5, wherein the supporting structure comprises a thermo-deformable material.

7. The application device according to claim 1, wherein the supporting structure comprises a plastic material, a thermoplastic material or a cured resin material.

8. The application device according to claim 7, wherein the supporting structure is at least partially adaptable to a back of the user's head while the material is not yet completely cured.

9. The application device according to claim 1, wherein the supporting structure comprises a material which is at least partially plastically deformable at temperatures of at least 30° C.

10. The application device according to claim 1, wherein the supporting structure is at least partially pre-shaped in accordance with an estimated shape of a back of the user's head.

11. The application device according to claim 1, wherein the cushion at least partially comprises a foamed and/or non-woven material.

12. The application device according to claim 1, wherein the cushion is at least partially embedded in a textile layer.

13. The application device according to claim 12, wherein the textile layer is configured so as to at least partially provide the coupling surface.

14. The application device according to claim 1, wherein the coupling of the supporting structure to the headband comprises a hook and loop fastener.

15. The application device according to claim 1, wherein the stiffening layer comprises at least one opening.

16. The application device according to claim 1, wherein the supporting structure is configured as a curved plate element.

17. The application device according to claim 1, wherein the supporting structure comprises lower leg portions to guide respective lower band portions of the headband.

18. A mask assembly for treating a user for sleep-related respiratory disorders, comprising:
   a breathing mask to supply a user with breathable gas; and
   an application device according to claim 17, wherein the lower band portions are adapted to extend in an application position across the user's cheekbones.

19. The application device according to claim 1, wherein the supporting structure comprises upper leg portions to guide respective upper band portions of the headband.

20. A mask assembly for treating a user for sleep-related respiratory disorders, comprising:
   a breathing mask to supply a user with breathable gas; and
   an application device according to claim 19, wherein the upper band portions are adapted to extend in an area of the user's forehead.

21. The application device according to claim 1, wherein the supporting structure is adapted to at least partially determine a course of the headband so as to increase the resistance of the headband against slipping and/or twisting.

22. A mask assembly for treating a user for sleep-related respiratory disorders, comprising:
   a breathing mask to supply a user with breathable gas; and
   an application device according to claim 1.

23. The application device according to claim 1, wherein the cushion is attached to both the stiffening layer and the coupling surface such that the cushion, the stiffening layer and the coupling surface are together removably attachable to the headband.

24. The application device according to claim 1, wherein the cushion is positioned between the stiffening layer and the cushion layer of the headband when the supporting structure is attached to the headband.

25. The application device according to claim 1, wherein stiffening layer is positioned outside of the cushion layer with respect to the user's face when the application device is worn by the user.

26. The application device according to claim 1, said headband further including a non-face contacting surface, wherein the cushion is disposed between the stiffening layer and the non-face contacting surface of the headband when the supporting structure is attached to the headband.

27. The application device according to claim 26, wherein the headband is configured to be attached to the breathing mask.

28. The application device according to claim 27, wherein the supporting structure connects only to the headband.

29. An application device for a breathing mask, comprising:
- a headband configured to support a breathing mask on a user's face, the headband including a cushion layer and a surface configured to contact the user's skin; and
- a supporting structure to facilitate the headband in supporting the breathing mask, the supporting structure comprising:
  - a stiffening layer;
  - a cushion located on an inner side of the supporting structure adapted to face the user in an application position; and
  - a coupling surface including an attachment structure configured to releasably couple the supporting structure with the headband such that the supporting structure is configured to be removably attachable to the headband,
- wherein the cushion is attached to both the stiffening layer and the coupling surface such that the cushion, the stiffening layer and the coupling surface are together removably attachable to the headband.

30. The application device according to claim 29, wherein the supporting structure comprises a plastic material, a thermoplastic material or a cured resin material.

31. The application device according to claim 29, wherein the cushion is at least partially embedded in a textile layer.

32. The application device according to claim 29, wherein the supporting structure comprises lower leg portions to guide respective lower band portions of the headband.

33. The application device according to claim 29, wherein the supporting structure comprises upper leg portions to guide respective upper band portions of the headband.

34. A mask assembly for treating a user for sleep-related respiratory disorders, comprising:
- a breathing mask to supply a user with breathable gas; and
- an application device according to claim 29.

35. An application device for a breathing mask, comprising:
- a headband configured to support a breathing mask on a user's face, the headband including a cushion layer and a surface configured to contact the user's skin; and
- a supporting structure to facilitate the headband in supporting the breathing mask, the supporting structure comprising:
  - a stiffening layer;
  - a cushion located on an inner side of the supporting structure adapted to face the user in an application position; and
  - a coupling surface including an attachment structure configured to releasably couple the supporting structure with the headband such that the supporting structure is configured to be removably attachable to the headband,
- wherein the cushion is positioned between the stiffening layer and the cushion layer of the headband when the supporting structure is attached to the headband.

36. The application device according to claim 35, wherein the supporting structure comprises a plastic material, a thermoplastic material or a cured resin material.

37. The application device according to claim 35, wherein the cushion is at least partially embedded in a textile layer.

38. The application device according to claim 35, wherein the supporting structure comprises lower leg portions to guide respective lower band portions of the headband.

39. The application device according to claim 35, wherein the supporting structure comprises upper leg portions to guide respective upper band portions of the headband.

40. A mask assembly for treating a user for sleep-related respiratory disorders, comprising:
- a breathing mask to supply a user with breathable gas; and
- an application device according to claim 35.

41. An application device for a breathing mask, comprising:
- a headband configured to support a breathing mask on a user's face, the headband including a cushion layer and a surface configured to contact the user's skin; and
- a supporting structure to facilitate the headband in supporting the breathing mask, the supporting structure comprising:
  - a stiffening layer;
  - a cushion located on an inner side of the supporting structure adapted to face the user in an application position; and
  - a coupling surface including an attachment structure configured to releasably couple the supporting structure with the headband such that the supporting structure is configured to be removably attachable to the headband,
- wherein stiffening layer is positioned outside of the cushion layer with respect to the user's face when the application device is worn by the user.

42. The application device according to claim 41, wherein the supporting structure comprises a plastic material, a thermoplastic material or a cured resin material.

43. The application device according to claim 41, wherein the cushion is at least partially embedded in a textile layer.

44. The application device according to claim 41, wherein the supporting structure comprises lower leg portions to guide respective lower band portions of the headband.

45. The application device according to claim 41, wherein the supporting structure comprises upper leg portions to guide respective upper band portions of the headband.

46. A mask assembly for treating a user for sleep-related respiratory disorders, comprising:
- a breathing mask to supply a user with breathable gas; and
- an application device according to claim 41.

* * * * *